United States Patent [19]

Liao et al.

[11] Patent Number: 5,208,263

[45] Date of Patent: May 4, 1993

[54] ANTI-ANDROGEN COMPOUNDS

[75] Inventors: Shutsung Liao; John Pataki; Ronald G. Harvey, all of Chicago, Ill.

[73] Assignee: Arch Development Corporation, Chicago, Ill.

[21] Appl. No.: 413,249

[22] Filed: Sep. 27, 1989

Related U.S. Application Data

[63] Continuation-in-part of Ser. No. 252,375, Sep. 30, 1988, abandoned.

[51] Int. Cl.$^5$ .................... A61K 31/045; A61K 31/04
[52] U.S. Cl. .................................. 514/730; 514/732;
560/141; 568/326; 568/714; 568/732; 568/733;
552/502; 552/650; 552/623
[58] Field of Search ............. 260/397.3, 397.4, 397.45,
260/397.5; 560/141; 568/326, 714, 732, 733;
514/730, 732

[56] References Cited

U.S. PATENT DOCUMENTS 3,992,437 11/1976 Shaw et al. .......................... 568/326
4,034,045 7/1977 Barcza et al. ....................... 568/326

FOREIGN PATENT DOCUMENTS 073931 11/1966 Japan .................................. 126/260
002497 1/1967 Japan .................................. 126/260

OTHER PUBLICATIONS

Chang et al. (1986), Endocrinology, 118A208.
Bingham, K. D., et al., J. Endocr., 57:111–121 (1973).
Chang, C., et al., J. Steroid Biochem., 27:123–131 (1987).
Fang, S., et al., The Journal of Biological Chemistry, 246:16–24 (1971).
Fang, S., et al., Mol. Pharmacol., 5:420–431 (1969).
Geller, J., et al., J. Clin. Endocrinol. Metabl., 43:686–688 (1976).
Gorski, J., et al., Ann. Rev. Physiol., 38:425–450 (1976).
Harvey, R. G., et al., J. Org. Chem., 51:1407–1412 (1986).
Huggins, C., et al., Cancer Res., 1:293–297 (1941).
Jensen, E. V., et al., Proc. Nat'l. Acad. Sci. (USA), 59:632–638 (1968).
Kuttenn, F., et al., J. Endocr., 75:83–91 (1977).
Lee, H., et al., J. Org. Chem., 53:4253–4256 (1988).
Liao, S., et al., Biochemistry of Steroid Hormones, 2nd edition, 17:633–680; Edited by H. L. J. Makin; (Blackwell Scientific Publication, Oxford (1984)).
Liao, S., Biochemical Actions of Hormones, 4:351–406; Edited by G. Litwack; (Academic Press, Inc., New York (1977)).
Liao, S., et al., Endocrinology, 94:1205–1209 (1974).
Liao, S., et al., The Journal of Biological Chemistry, 248:6154–6162 (1973).
Liao, S., et al., Proc. Nat'l. Acad. Sci. (USA), 82:8345–8348 (1985).
Martini, L. and Motta, M. Androgens and Antiandrogens, Raven Press, New York, New York (1977). [table of contents only].
Neri, R. O., Androgens and Antiandrogens, p. 179, Raven Press, New York, New York (1977).
Neumann, F., et al., Androgens and Antiandrogens, p. 163, Raven Press, New York, New York (1977).
Sansone, G., et al., The Journal of Investigative Dermatology, 56:366–372 (1971).
Schilling, K., et al., The Prostate, 5:581–588 (1984).
Siiteri, P. K., et al., The Journal of Clinical Investigation, 49:1737–1745 (1970).
Stork, G., et al., J. Am. Chem. Soc., 85:2178–2180 (1963).
Whitesell, J. K., et al., Synthesis, 7:517 (1983).

*Primary Examiner*—Frederick E. Waddell
*Assistant Examiner*—Frederick F. Tsung
*Attorney, Agent, or Firm*—Arnold, White & Durkee

[57] ABSTRACT

Disclosed are novel classes of anti-androgen including dihydrophenanthrene derivatives, their method of synthesis and their use in treating disorders associated with excessive androgenic activities.

1 Claim, 4 Drawing Sheets

ANTI-ANDROGEN COMPOUNDS

The Unites States Government may have certain right in the present invention pursuant to grant number NIH-DDKD DK 37694.

CROSS REFERENCE TO RELATED APPLICATIONS

The present invention is a continuation-in-part of co-pending U.S. patent application Ser. No. 07/252,375, filed Sep. 30, 1988, now abandoned.

BACKGROUND OF THE INVENTION

The present invention relates generally to new classes of anti-androgen compounds, their method of synthesis and their use as anti-androgens.

Androgens are one of the five major classes of steroid hormones. Steroid hormones form complexes with receptor proteins which are distributed in a tissue specific fashion within target cells. Jensen, et al., *Proc. Nat'l. Acad. Sci. (USA)*, 59:632 (1968); Gorski, et al., *Ann. Rev. Physiol.*, 42:17 (1976); and Liao, et al., page 633 in *Biochemistry of Hormones*, H.L.J. Makin, ed. (Blackwell Sci. Publ. Oxford, 1984). Investigation of the specificity and affinity of steroid hormones for their particular cellular receptors(s) has contributed greatly to the understanding of the relationship between structure and biological activity, target organ specificity, overlaps in hormonal activity, and the mechanism of action of many anti-hormones. Liao, S., et al., *J. Biol. Chem.*, 248:6154 (1973); Liao, S., *Biochemical Actions of Hormones* (Litwack, G., ed), 4:351, Academic Press, New York (1977); Liao, et al., *Biochemistry of Steroid Hormones*, (Makin, H.L.J., ed.) pp. 630–680, Blackwell Scientific Publications, Oxford (1984).

Studies on the structural recognition of ligands by steroid receptors suggests that compounds with geometric structures similar to that of natural androgens, such as 5α-dihydrotestosterone, can bind tightly to androgen receptors and can act either as potent androgens or as anti-androgens. Liao, S., et al., *J. Biol. Chem.*, 248:6154 (1973). The most well known steroidal anti-androgens are cyproterone and its acetate [(Neumann, *Androgens and Anti-androgens*, (L. Martini and M. Motta, ed.) pp. 163, Raven Press, New York (1977)]which act by interacting with androgen receptors and prevent androgens from binding to the receptors. Fang, S., *Molec. Pharmacol.*, 5:428 (1969). Nonsteroidal anti-androgens, such as flutamide-related compounds, also act through the same mechanism. Liao, S., et al., *Endocrinol.*, 94:1205 (1974) and Neri, R., *Androgens and Anti-androgens*, (L. Martini & M. Motta, ed.) pp. 179, Raven Press, New York (1977).

Studies of the topographic recognition of cyclic hydrocarbons and related compounds by receptors for various steroid hormones have suggested that while the hormonal action of a steroid may be dependent upon the interaction of a functional group present on the hormone with a specific group present on the receptor, the presence of such a functional group may not be required for the antagonistic activities of a compound that can physically block hormone binding to the receptor. Thus, many small molecules, that were hitherto considered to be biologically inert, may interact with steroid receptors specifically and affect hormonal activities in vivo. Chang, C., et al., *J. Steroid Biochem.*, 27:123 (1987). One such example is 9,10-dihydrophenanthrene (DHP) which, in comparison to a natural androgen, lacks one of the rings as well as two functional groups, including a double-bonded oxygen and a hydroxyl group. Despite these differences, DHP nevertheless interacts with androgen receptors in cell-free systems and inhibits the growth of the ventral prostate in rats. Chang, C., et al., *J. Steroid Biochem.*, 27:123 (1987).

Currently, potent anti-androgenic compounds, such as cyproterone and its acetate, and flutamide, are not used in the United States of America because of their side effects, including undesired hormonal activities and/or toxicities.

Thus, there continues to exist a need in the art for new classes of anti-androgens which do not have other hormonal activities and/or side effects, yet, which are useful in treating diseases or abnormalities related to androgen responsive organs.

BRIEF SUMMARY OF THE INVENTION

The present invention relates generally to novel classes of anti-androgens comprising a compound of the general formula:

wherein said ring A is substituted or unsubstituted and wherein when said ring A is substituted it is fused at either the 1-2 or 2-3 positions to a hydroxycycloalkyl, or a ketocycloalkyl, or is substituted with a hydroxyl, an alkyl, or a hydroxyalkyl at the 1, 2, or 3 positions;

wherein said ring B is saturated or mono-unsaturated at the 9-10 position and is optionally substituted with a lower alkyl at either the 9 or 10 position;

wherein said ring C is substituted or unsubstituted, and wherein when said ring C is substituted it is fused at the 6-7 or 7-8 positions to a ketocycloalkyl or a hydroxycycloalkyl; and provided that rings A and C may not both be unsubstituted. Preferably, the ketocycloalkyl is a cyclopentanone or cyclohexanone; the hydroxycycloalkyl is cyclopentanol or cyclohexanol, and the alkyl is methyl.

Preferred derivatives include 1-[2-(9,10dihydrophenanthryl)]-1-ethanol; 6,7,16,17-tetrahydro15H-cyclopenta[a]-phenanthren-17-ol; 1-[2-(9(or 10)-methyl-9,10-dihydrophenanthryl)]-1-ethanol; 2-hydroxy-9,10-dihydrophenanthrene; 6,7,16,17-tetrahydro-15Hcyclopenta[a]pehanthren-17-one; 4'-oxo-7,8-cyclohexeno9,10-dihydrophenanthren-1-ol; and 4'-oxo-7,8-cyclohexenophenanthren-1-ol. Also provided by the invention are the corresponding derivatives wherein a free hydroxyl group has been replaced with an acetate or a propionate moiety.

Also provided by the invention are pharmaceutical compositions comprising pharmaceutically effective amounts of one or more compounds of the invention in combination with a pharmaceutically acceptable solvent, diluent, adjuvant, or carrier, as well as methods for treatment of disorders associated with excessive androgenic activities by administering compounds of the invention, alone or in combination, or as pharmaceutical compositions.

In one preferred embodiment of the present invention, a therapeutically effective amount of one or more of the compounds of the invention can be administered to treat various disorders including those conditions wherein excessive androgenic activities have been implicated in the pathogenesis of certain androgen dependent conditions, such as benign prostatic hyperplasia, prostate cancer, male pattern baldness, female hirsutism, and the like. These pharmaceutical compositions, comprising compounds of the invention, can be administered by topically or internal routes.

In addition, it is expected that some of the compounds of the invention may interact with mutated receptors and, therefore, may be useful in the treatment, as well in the diagnosis of, androgen and other hormone-insensitive tumors. It is also expected that compounds of the invention will be important in the studies of the mechanism of action of androgens and anti-androgens. Thus, also provided by the invention are methods for localizing androgen receptors in, for example, tissue samples, wherein the sample is incubated with a compound of the invention and wherein the compound is labelled with a marker, the marker is detected and the androgen receptor in the sample is thereby localized.

Other aspects and advantages of the present invention will be apparent upon consideration of the following detailed description thereof which includes numerous illustrative examples of the practice of the invention, reference being made to the drawing wherein:

DETAILED DESCRIPTION

The following examples illustrate practice of the invention in the synthesis of new classes of anti-androgen compounds and their activity and use as anti-androgens. More specifically, Example 1 relates to the synthesis of the compounds of the invention and Example 2 relates to a comparison of the relative binding activities of the compounds of the invention.

The examples which follow are for illustrative purposes only and are not intended in any way to limit the scope of the invention.

EXAMPLE 1

Structural Considerations and Synthesis of Dihydrophenanthrene Derivatives

Among the requirements considered in constructing the new classes of anti-androgens were the following. Preferably, the geometry of the ligand molecule should be the same as, or smaller, than natural androgens, such as $5\alpha$-dihydrotestosterone, so that the molecule can be easily inserted into the ligand binding site of the receptor and can have a high rate of association. In contrast to natural steroid hormones that have a rigid structure, the molecule preferably should have a flexible structure allowing it to conform to the structure of the receptor binding cavity and to become trapped. This results in a ligand with a high binding affinity and with a slow rate of dissociation. It is also preferable, but possibly not essential, that the molecule have a functional group present, at one or both ends of the molecule, that corresponds to the carbonyl group of ring-A and/or the hydroxyl group of ring-D of a natural androgen. It is also preferable that the molecule be able to interact or to bind to the receptor in a cell-free assay, in an organ or cell-binding assay, or in an in vivo biological assay.

A number of classes of compounds were synthezied following the above guidelines. These general classes include dihydrophenanthrene derivatives and chrysene derivatives. Their sythesis is described below. See also, Lee, H., et al., *J. Org. Chem.*, 53:4253 (1988) and Harvey, R., et al., *J. Org. Chem.*, 51:1407 (1986).

Figure 1:
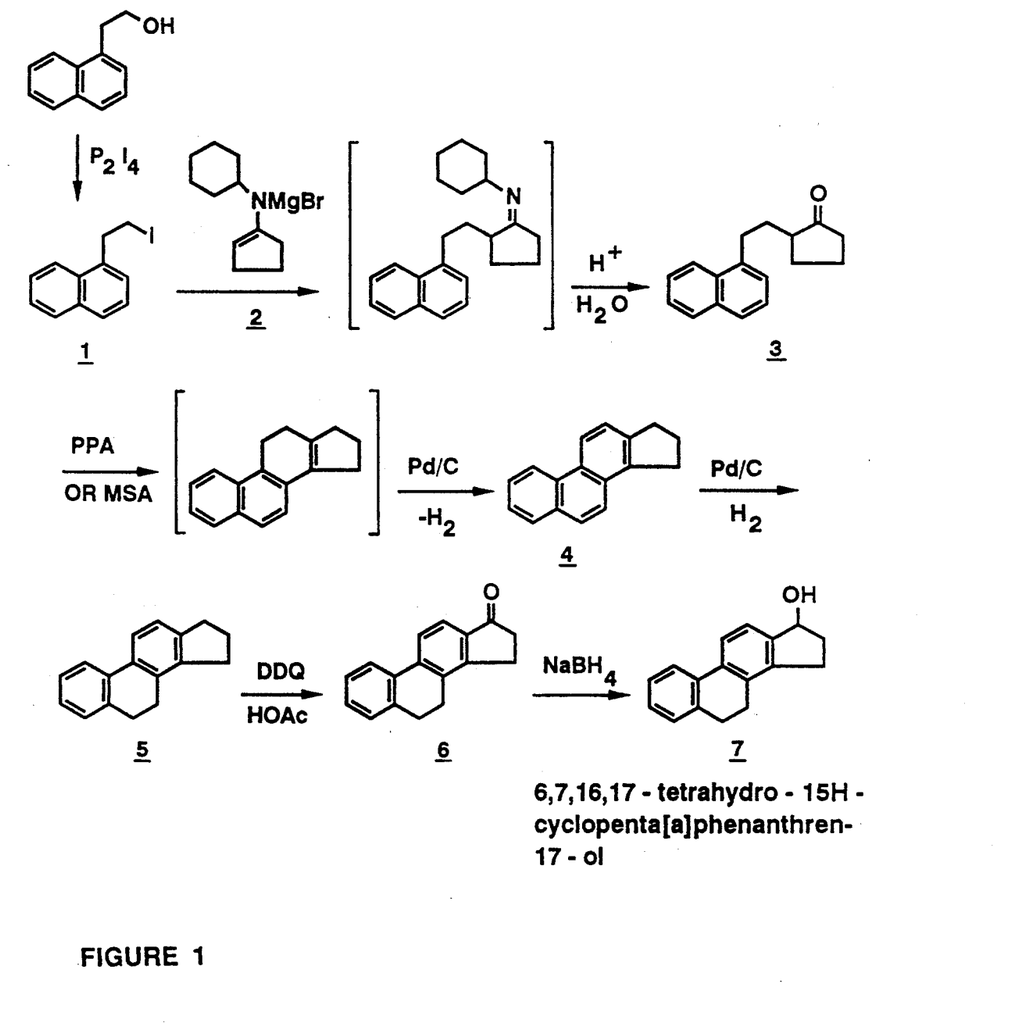
FIG. 1 is a schematic representation of the synthesis of compounds 1, 3, 4, 5, 6, and 7.

Shown in FIG. 1 is a schematic representation of the synthesis of intermediates 1, 3, 4 and dihydrophenanthrene derivatives 5, 6 and 7, as described below.

2-(1-Naphthyl)ethyl iodide (1)

To a solution of $P_2I_4$ (7 878 g; 13.82 mmol) in $CS_2$ (350 ml) was added at once 2-naphthalen-ethanol. The mixture was stirred for 48 h. The solvent was evaporated and the residue was dissolved in ether. The ether solution was extracted with water 3 times. Column chromatography on Florisil TM afforded (1) as an oil (10 g, 67%).

2-[2-(1-Naphthyl)ethyl]cyclopentanone (3)

To a solution of (2) N-cyclohexyl-N-cyclopentenyl magnesium bromide, prepared from the reaction of N-cyclopentylidenecyclohexylimine [See Whitesell, J.K.,; Whitesell, M.A., *Synthesis*, page 517 (1983); and Stork, G., et al., *J. Am.-Chem.-.Soc.*, 85:2178 (1963)](8.5 g, 415 mmol) with ethylmagnesium bromide (60 mmol; 10 mL of 3 mole solution in THF) was added 2-(1-naphthyl)ethyl iodide (1) (12 g; 42 mmol), and the resulting mixture was refluxed for 20 h. Hydrolysis was effected by refluxing with 180 mL of 10% aqueous HCl for 3 h. The product was extracted and further purified by chromatography on a column of Florisil TM, Floridin Co., Florida. Elution with benzene afforded (3) (9.68 g; 96%) as an oil:NMR, $\delta 1.3$-2.5 (m,8,aliphatic), 3.1 (apparent,2,benzylic), 7.2–8.2 (m,7,aromatic). Anal. Calc'd. for $C_{17}H_{18}O$: C,85.67; H,7.61; Found: C,85.72; H,7.63.

16,17-Dihydro-15-cyclopenta[a]pheanthrene (4)

Cyclization of (3) (6.4 g; 26 mmol) was carried out in polyphosphoric acid (10 ml) at 110° C. for 2 h under $N_2$. Ice water was added, and the mixture was extracted with $CH_2Cl_2$. The product was worked up conventionally and chromatographed on a column of Florisil TM to yield a mixture of (4) and other products of acidic disproporationation. This mixture was dehydrogenated by heating with 10% Pd/C (1.8 g) in triglyme (250 ml) at reflux for 2 h under $N_2$. The reaction mixture was cooled and filtered, and the filtrate was diluted with ether and washed with water several times to remove triglyme. The ether solution was dried over $MgSO_4$ and evaporated to dryness to afford a white solid which was triturated with cold hexane to yield pure (4) (14.9 g, 85%):mp 134°–135° C.; NMR 2.27 (m,l,$H_2$or$_3$), 7.72 (s,2,$H_{6,7}$), 7.85 (m,l,$H_4$,8.50 (d,l,$H_{11,12}$=8.2 Hz), 8.64 (m,l,$H_1$).

6,7,16,17-Tetrahydro-15Hcyclopenta[a]phenanthrene (5)

Compound (4) (4.3 g; 19 mmol), dissolved in ethyl acetate (100 ml), was hydrogenated over a 10% Pd/C catalyst (3.2 g) at 50 lb/sq.i. pressure at room temperature for 24 h. Crystallization from hexane gave compound (5) as a white solid (2.97 g, 71%):m.p. 64-65%; NMR; δ2.2 (m,2,aliphatic), 2.7-3.2 (m,8,benzylic), 7.1-7.4 (m,4,aromatic), 7.6 (d,1,H$_{11}$), 7.7 (m,1,H$_1$)

6,7,16,17-Tetrahydro-15H-cyclopenta[a]phenanthren-17-one (6)

The hydrocarbon (5) 48 mg; 0.22 mmol) was dissolved in hot acetic acid (15 ml) and water (5 ml) was added slowly with stirring to maintain homogeneity of the solution. 2,3-Dichloro-5,6-dicyano-1,4-benzoquinone (DDQ) (198 mg, 0.88 mmol) was added, changing the color of the solution to dark green. Stirring was continued at reflux for 30 min. during which time the color of the solution changed to dark red. The reaction mixture was cooled and diluted with ether, and the ether layer was washed with water and aqueous NaOH. The solution was dried over MgSO$_4$ and evaporated to provide a white solid which was chromatographed on a column of Florisil TM. Elution with ether yielded 6 (39 mg, 76%):m.p. 127°-128° C.; NMR δ272 (t,1,H$_{15}$or$_{16}$), 2.85-2.91 (m,4,H$_{6,7}$), 3.07 (t,1,H$_{15}$or$_{16}$), 7.24-7.31 (m,3,H$_{2,3,4}$), 7.67-7.77 (m,3,H$_{1,11,12}$) Anal. Calc'd. for C$_{17}$H$_{14}$O: C,87.25; H,6.02. Found: C,87.13; H,6.03.

6,7,16,17-Tetrahydro-15H cyclopenta[a]pehanthren-17-ol (7)

A suspension of ketone (6) (300 mg) and NaBH$_4$ (200 mg) in MeOH (500 ml) and THF (30 ml) was stirred at room temperature for 2.5 h. Solvents were evaporated and the residue was taken up in ether. The ether solution was washed with H$_2$O three times. Column chromatography on Florisil TM afforded (7) (290 mg; ≧98%) as a solid, NMR; δ2.8 (m,8,H$_{6,7,16,15}$), 7.8 (m,6,aromatics).

Figure 2:
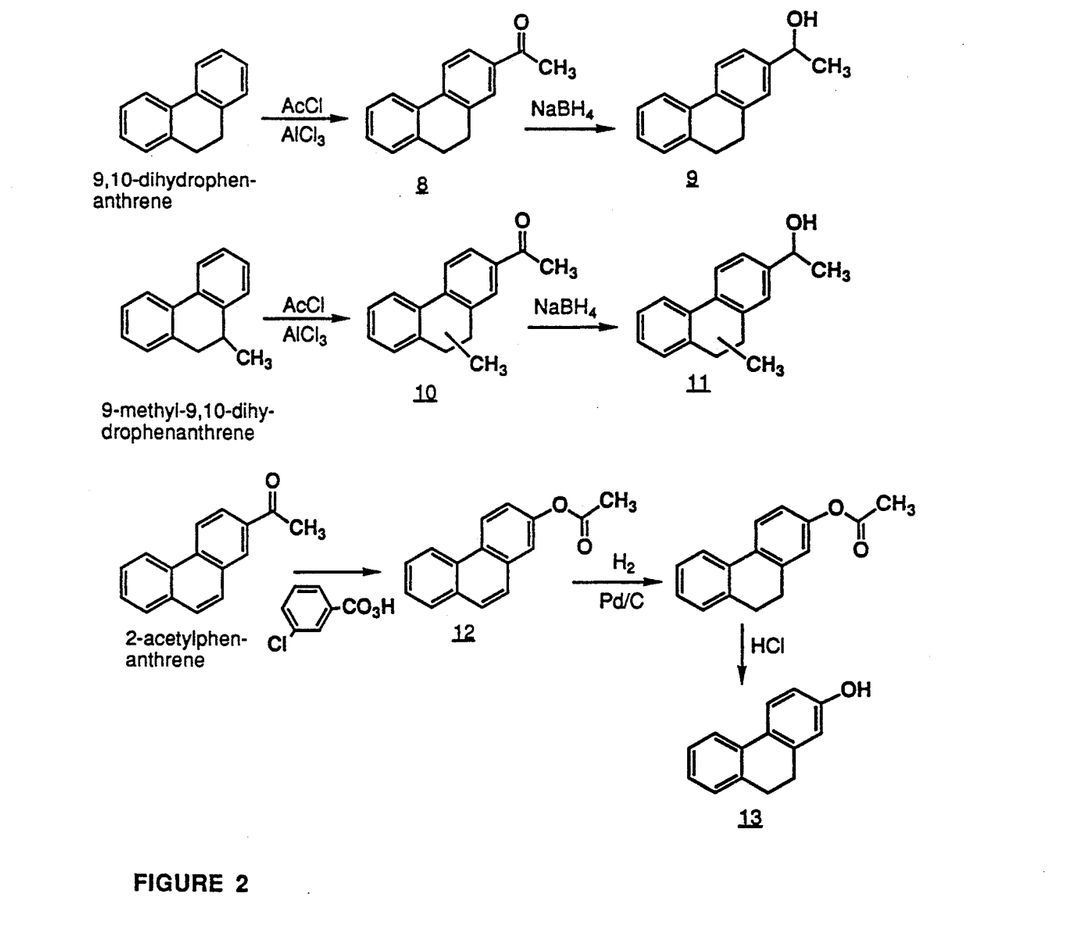
FIG. 2 is a schematic representation of the synthesis of compounds 8, 9, 10, 11, 12, and 13.

Shown in FIG. 2 is a schematic representation of the synthesis of dihydrophenanthrene derivatives 8, 9, 10, 11, 12, and 13, as described below.

2-Acetyl-9,10-dihydrophenanthrene (8)

To a solution of 18 g (0.1 mole) 9,10-dihydrophenanthrene in 200 mL of dry CH$_2$Cl$_2$, cooled in ice, 20 g (0.15 mole) of anh. AlCl$_3$ was added. To this solution 9.42 g (0.12 mmole) of acetyl chloride in 50 mL of dry CH$_2$Cl$_2$ was added in 17 mins. Stirring was continued for 30 mins in ice and 2 h at room temperature. The solution was poured on ice and 25 mL of concentrated HCl and stirred for 15 mins. The yellow organic layer was separated, washed with NaHCO$_3$ solution, and dried. The solvent was removed and the residue distilled at 0.15 mm pressure. The distillate, 15.28 g, crystallized from ethanol-hexane, m.p. 58°-60°.

1-[2-(9,10-Dihydrophenanthryl)]-1-ethanol (9)

To a stirred solution of 1.0 g of 2-acetyl9,10-dihydrophenanthrene in 35 mL of MeOH was added 1 g of NaBH$_4$ in small portions within 45 mins. The solution was stirred for 2 h more. Most of the MeOH was removed under reduced pressure. Water was added to the residue, and the residue was extracted twice with CH$_2$Cl$_2$; the combined two extracts were dried and evaporated to dryness. The residue crystallized from ether, m.p. 84°-85.5°.

2-Acetyl-9(or 10)-methyl-9,10dihydrophenanthrene (10)

To a stirred solution of 5.216 g (26.86 mmol) of 9-methyl-9,10-dihydrophenanthrene in 100 mL of dry CH$_2$Cl$_2$, cooled in an ice-salt bath, 6.67 g (50 mmol) of anh. AlCl3 was added. To the deep red solution, a solution of 2.2 mL (2.402 g; 32.23 mmol) of acetyl chloride in 25 mL of dry CH$_2$Cl$_2$ was added dropwise in 20 mins. The solution was stirred 30 mins in a cooling bath and for 2 h at room temperature. The mixture was poured on ice and 10 mL of concentrated HCl and stirred for 15 mins. The organic layer was separated, washed with H$_2$O and saturated brine, and dried. The solvent was removed and the residue chromatographed on Florisil TM Hexane-ether (9:1) eluted 3.37 g of the oily title compound.

1-[2-(9-(or 10)-Methyl-9,10dihydrophenanthryl}]-1-ethanol (11)

To a stirred solution of 980 mg of 2-acetyl-9(or 10-)methyl-9,10-dihydrophenanthrene (10) in 40 mL of MeOH, 1 g of NaBH$_4$ was added in small portions within 45 mins and stirring was continued for 2 h more. About 30 mL of MeOH was distilled off under reduced pressure. The residue was taken up in CH$_2$Cl$_2$; the solution was washed with H$_2$O and dried; and the solvent was removed. The title compound (944 mg) was obtained as an oil.

2-Acetoxyphenanthrene (12)

A solution of 2.2 g (10 mmol) of 2-acetylphenanthrene in 50 mL of CH$_2$Cl$_2$ was stirred with 3.45 g (20 mmol) of m-chloro-peroxybenzoic acid for 3 h and allowed to stand for 93 h at room temperature. The solution was washed twice with 5% KOH solution and once with H$_2$O, was dried and the solvent removed. From MeOH there was obtained 1.52 g of the title compound, m.p. 141°-142.5°.

2-Hydroxy-9,10-dihydrophenanthrene (13)

One gram of 2-acetoxyphenanthrene was hydrogenated in 30 mL of ethyl acetate with 0.5 g of 10% Pd/C catalyst for 120 h at 35 lb/sq.i. pressure. The catalyst was filtered off and washed with ethyl acetate. The filtrate was evaporated to dryness.

The product obtained from the hydrogenation was dissolved in 50 mL of MeOH, 1 mL of concentrated HCl was added and the solution was allowed to stand for 23 h at room temperature. Two grams of NaOAc was added, the NaCl filtered off and most of the solvent was removed from the filtrate. The residue was dissolved in EtOAc, the solution washed with NaHCO$_3$ solution, dried, and the solvent was removed under reduced pressure. The residue (943 mg) was chromatographed on Florisil TM. Hexane-benzene (6:4) eluted 480 mg of the oily 2-hydroxy-9,10-dihydrophenanthrene.

Figure 3:
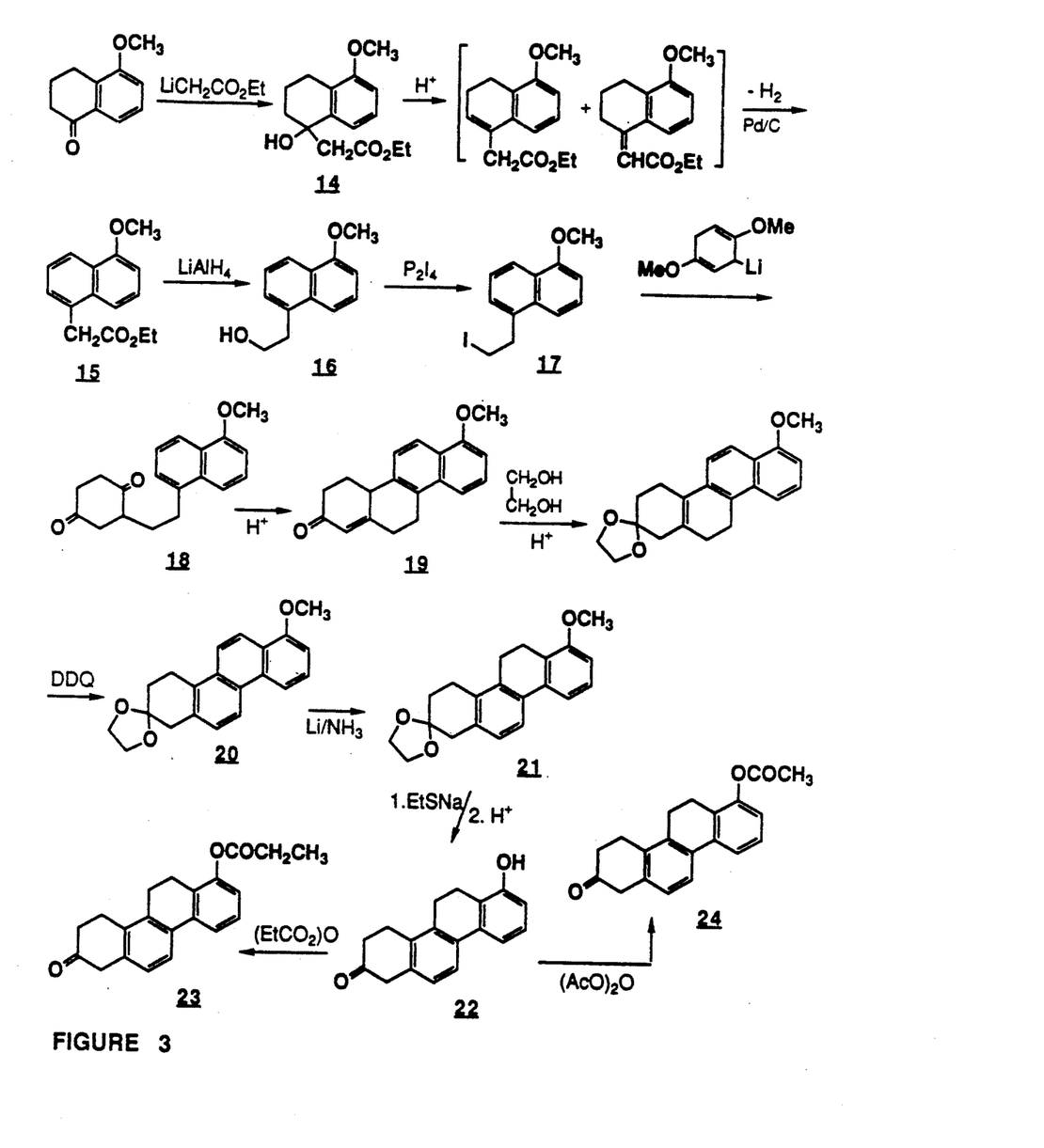
FIG. 3 is a schematic representation of the synthesis of compounds 14, 15, 16, 17, 18, 19, 20, 21, 22, 23, and 24.

Shown in FIG. 3 is a schematic representation of the synthesis of compounds 14, 15, 16, 17, 18, 19, 20, 21, 22, 23, and 24, as described below. Also described below is the synthesis of derivative 25.

Ethyl 1-Hydroxy-5-methoxy-1,2,3,4-tetrahydronaphthanlene-1-acetate (14)

To 300 mL of 1M lithium bis(trimethylsilyl)amide in THF, 26.43 g (0.3 mole) of dry ethyl acetate was added dropwise at −78° C. under N$_2$. The solution was stirred for 15 mins, then a solution of 52.87 g (0.3 mole) of 5-methoxy-1-tetralone in 200 mL of dry THF was added over 40 mins. Stirring was continued for 10 mins more, then 75 mL of 20% HCl was added over 10 mins. The mixture was allowed to come to room temperature, then the organic layer was diluted with benzene, and washed with $H_2O$. After drying, the solvents were removed under reduced pressure. The residue crystallized upon addition of hexane to yield the title compound, 62.17 g (m.p. 57°–58° C.), second crop, 12.80 g (m.p. 50°–53° C.) yield 94.4%.

Ethyl 5-Methoxynaphthalene-1-acetate (15)

The above ester (14) 74.9 g was heated at reflux in 60 mL of benzene with 600 mg of TsOH for 30 mins. The solution was cooled, washed with $NaHCO_3$ solution, and dried. Evaporation of the solvent left 69.4 g (99.5%) of an oily mixture of products with the newly formed double bound in the endocyclic and exocyclic positions.

A solution of the above product in 1400 mL of triethylene glycol dimethyl ether was heated at reflux with 30 g of 10% palladium-carbon catalyst under $N_2$ for 2 h. The mixture was cooled, the catalyst filtered off, and the filtrate was diluted with 3600 mL of ice-water and allowed to stand in the cold overnight. The crystals were filtered off, washed with $H_2O$, and dried. After stirring with 60 mL of EtOH, the colorless crystals were filtered off and dried to yield the title compound (47.4 g, 68.3%) melting at 62.5°–65.6° C., m.p. of a recrystallized sample 67.5°–68.5° C.

1-(2-Hydroxyethyl)-5-methoxynaphthalene (16)

To a stirred suspension of 3 g (0.08 mole) of $LiAlH_4$ in 100 mL of dry $Et_2O$, a solution of 30 g (0.12 mole) of ethyl-5-methoxy-naphthalene-1-acetate in 400 mL of dry $Et_2O$ was added over 135 mins under $N_2$. The mixture was stirred for 2 h, cooled in ice, and decomposed by dropwise addition of 20 mL of satd. aq. $Na_2SO_4$ solution. The precipitate was filtered off and washed with $Et_2O$. After evaporation of the solvent a crystalline product remained that was stirred with cold hexane. The alcohol (21.95 g, 90.5%) melted at 61°–62° C.

1-(2-Iodoethyl)-5-methoxynaphthalene (17)

To a solution of 18.4 g (0.032 mole) of $P_2I_4$ in 600 mL of dry $CS_2$, a solution of 21.9 g (0.108 mole) of the above alcohol (16) in 250 mL of $CS_2$ was added at 0° C. under $N_2$. The dark solution was stirred at room temperature for 120 h. Solid $K_2CO_3$ (25 g) and 140 mL of satd. $K_2CO_3$ solution were added and the mixture was stirred for 20 mins. The organic layer was separated, dried, and the solvent removed. The residue was absorbed on 125 g of Florisil ™. The column was eluted with 1200 mL of hexane to yield the crystalline iodo compound (24.80 g, 73.6%) melting at 45°–47° C.

2-[2-(5-Methoxy-1-naphtyl)ethyl]cyclohexan-1,4-dione (18)

The solution of 48.9 mL (88 mmol) of 1.8 M t-BuLi in 450 mL of dry THF, cooled to −78° C., and 12.34 g (88 mmol) of 1,4-dimethoxycyclohexa-1,4-diene was added under $N_2$. After stirring for 1 h, 16 mL (92 mmol) of hexamethylphosphoramide (HMPA) was added and the deep red solution was stirred for 10 mins. The iodo compound (24 g, 77 mmol) (17) in 75 mL of dry THF was then added over 5 mins. After stirring 10 more mins, the solution was decomposed with 150 mL of saturated brine and extracted twice with hexane. The extracts were washed twice with 75 mL portions of brine, combined, dried and the solvents were removed under reduced pressure at 40° bath temperature.

The residue (25.23 g) was dissolved in 500 mL of acetone, the solution purged with $N_2$ for 20 mins and 167 mL of 1 N HCl, purged previously with $N_2$, was added to the vigorously stirred solution. Stirring was continued for 1 h. The acetone was removed under reduced pressure and the cooled residue was extracted twice with $CH_2Cl_2$. The extracts were washed with $H_2O$ dried, and the solvent was removed. The residue was stirred with warm MeOH, the insoluble material (1.39 g, m.p. 179°–184° C.) was filtered off and the filtrate evaporated to dryness. The residue was crystallized from $Et_2O$ to yield the title compound (15.61 g, 68.4%), m.p. 94°–100° C. A recrystallized sample melted at 100°–101.5° C.

1-Methoxy-5,6,10,10a-tetrahydro-8(9H)benzo[a]-phenanthrene-8-one (19)

To a stirred solution of 15 g of the above di-ketone (18), in 1500 mL of $Ch_2Cl_2$, 100 mL (151 g) of $MeSO_3H$ was added over 50 mins under $N_2$. Stirring was continued for 10 h more. The solution was poured on ice, and the organic layer was washed twice with $H_2O$ and dried. The residue was stirred with 40 mL of benzene. The $\alpha,\beta$-unsaturated ketone (9.50 g, 67.5%) had a melting point of 172°–177.5° C. A recrystallized sample (acetone) melted at 177°–179° C.

Ethylene ketal of 1-methoxy-4'-oxo-7,8-cyclohexeno-phenanthrene (20)

The above ketone (38.2 g) (19) in 1300 mL of benzene was heated at reflux with 2.6 g of TsOH and 55 mL of ethylene glycol for 21 h using a Dean-Stark trap. After cooling, the solution was washed with $NaHCO_3$ solution, dried, and the solvent removed to give 44.06 g (100%) of the ethylene ketal of 1-methoxy-5,6,10,10a-tetrahydro-8(9H)benzo[a]phenanthrene-8-one (19) which was dissolved in 1000 mL of dry benzene and heated at reflux with 36 g (1.1 equiv.) of DDQ for 15 mins under $N_2$. After cooling, the hydroquinone was filtered off and washed with benzene. The filtrate was concentrated to 500 mL and filtered through a column of 350 g of Florisil ™. The column was eluted with a total of 4 L of benzene to yield the dehydrogenated compound (39.1 g, 89.4%), m.p. 162°–163° C. (from acetone with a few drops of pyridine).

Ethylene ketal of 1-methoxy-4'-oxo-7,8-cyclohexeno-9,10dihydro-phenanthrene (21)

To 350 mL of anhydrous liquid $NH_3$ and 300 mg of dry $FeCl_3$, a solution of 10.00 g (31.2 mmol) of the above tetrahydro ketal (20) in 400 mL of dry THF was added with stirring under He. Li wire (1.080 g; 155.8 mg-atome; 5 equiv.) was added in small pieces. The ammonia was allowed to reflux for 1 h. The reaction was quenched with $NH_4Cl$ and the mixture poured on ice. The mixture was extracted twice with $CH_2Cl$, the extracts washed twice with $H_2O$, combined, dried, filtered through Celite and the solvent was removed under reduced pressure.

The residue, 9.06 g, in 250 mL of benzene was heated at reflux with 10 mL of ethylene glycol and 500 mg of TsOH for 22 h under $N_2$ using a Dean-Stark water trap. After cooling, the solutin was washed with $NaHCO_3$, dried, reduced to a small volume and adsorbed on 100 g of Florisil TM. The column was eluted with benzene. The eluted material was crystallized from Et₂O to yield (5.89 g, 58%) of the compound (21) m.p. 109°–110° C.

4'-oxo-7,8-cyclohexeno,9,10-dihydrophenanthren-1-ol (22)

To a stirred solution of 5.59 g (90 mmol) of EtSH in 40 mL of dry DMF, cooled in ice, 2.16 g (3.60 g of 60% oil dispersion; 90 mmol) of NaH was added under N₂. After the vigorous reaction subsided, the mixture was stirred at room temperature for 15 mins. A solution of 2.90 g (9 mmol) of the above ethylene ketal (21) in 40 mL of dry DMF was added, and the mixture was heated at reflux for 1 h. The mixture was poured into ice-water and extracted twice with EtOAc; the extracts were washed twice with H₂O, dried, and the solvent was removed. The residue was adsorbed on 30 g of Florisil TM. The column was washed with hexane to remove the oil and then eluted with benzene-Et₂O (85:15) to give 2.36 g of the demethylated product. The product was dissolved in 40 mL of acetone, the solution purged with N₂, 400 mg of TsOH was added, and the solution stirred for 4 h under N₂. Part of the ketone separated during the reacton. Water (80 mL) was slowly added, and the crystals were filtered off, washed with acetone H₂O, and dried to give 1.92 g (80.7%) of the free ketone, m.p. 242°–247° C.

4'-oxo-7,8-cyclohexeno,9,10-dihydrophenanthren-1-ol Propionate (23)

Sixty-five mg of 4'-oxo-7,8-cyclohexeno,9,10-dihydrophenanthren-1-ol (22) was dissolved in 2 mL of dry pyridine and 1 mL of propionic anhydride. The solution was allowed to stand 20 h at room temperature and was then poured into ice water. The mixture was extracted with benzene, the extract was washed with 1N HCl and 5% NaHCO₃ solution and dried. The colored solution was filtered through a short column of Florisil TM and the filtrate evaporated to dryness to give 62 mg of crystalline propionate.

4'-oxo-7,8-cyclohexeno,9,10-dihydrophenanthren-1-ol Acetate (24)

Fifty mg of 4'-oxo-7,8-cyclohexeno,9,10-dihydrophenanthren-1-ol (22) in 1.5 mL of dry pyridine and 0.5 mL of acetic anhydride was set aside for 24 h at room temperature and was then poured into ice water. The mixture was extracted with benzene, the extract was washed with 1 N HCl and 5% NaHCO₃ solution, dried and filtered through a short column of Florisil TM. Evaporation of the solvent under reduced pressure left 50 mg of crystalline acetate.

4'-oxo-7,8-cyclohexenophenanthren-1-ol (25)

To a stirred solution of 621 mg (10 mmol) of EtSH in 5 mL of anh., dimethylformamide, cooled in ice, 240 mg (10 mmol) of NaH was added under N₂. The mixture was stirred at room temperature for 15 mins. A solution of 320 mg (1 mmol) of compound (20) in 5 mL of anh. dimethylformamide was added and heated at reflux for 1 h. The mixtgure was poured on ice, extracted with benzene, the extract was washed twice with H₂O, dried, and the solvent removed. The residue was adsorbed on Florisil TM. Benzene-ether (25:15) eluted 285 mg of material which was dissolved in 8 mL of acetone. Fourty mg of tosic acid was added and the solution stirred for 4 h at room temperature. Water was added and the precipitated produce (25) was filtered off, washed with acetone-H₂O (1:1) and dried.

Figure 4:
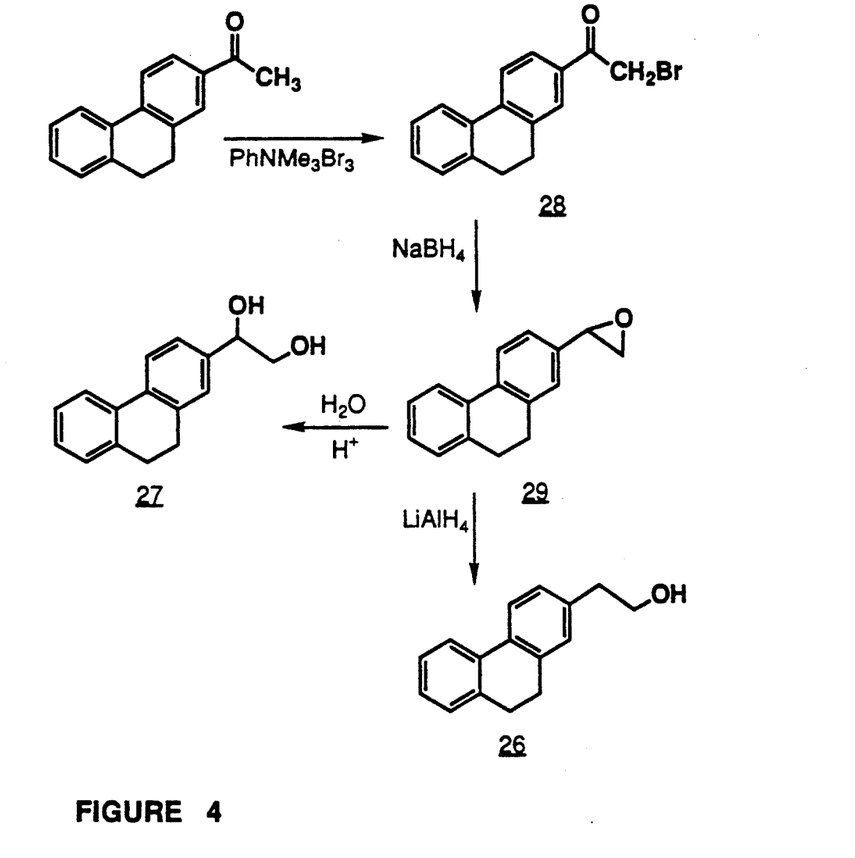
FIG. 4 is a schematic representation of the synthesis of compounds 26, 27, 28, and 29.

Shown in FIG. 4 is a schematic representation of the synthesis of compounds 26, 27, 28, and 29 as described below.

2-Bromoethyl-9,10-dihydrophenanthrene (28)

To a stirred solution of 5.56 (25 mmol) of (8) in 100 mL of THF, 9.78 g (26 mmol) of phenyltrimethylammonium tribromide was added. After stirring for 20 min, the solution became pale yellow and a precipitate of phenyltrimethylammonium bromide separated. Water (300 mL) was added and the mixture was extracted with ethyl acetate. The extract was washed with water and evaporated to dryness to yield (28) which was further purified by trituration with ether and recrystallized from methanol to furnish pure (28), 5.66 g; m.p. 82°–83° C.

2-Oxiranyl,9,10-dihydrophenanthrene (29)

To a boiling solution of 1.51 g (5 mmol) of (28) in ethanol (40 mL), a solution of 285 mg (7,5 mmol) of NaBH₄ in 5 mL of water was added dropwise. Boiling was continued for 5 min, the solution was cooled, diluted with water, and extracted with ether. The ether extract was washed with water, dried, and the solvent was removed at reduced pressure to provide (29) as a colorless oil. This soldified on trituration with a few drops of ether to yield (29), m.p. 65°–66° C.

2-[2-(9,10-dihydrophenanthryl)]-1-ethanol (26)

A solution of (29) (778 mg, 3.5 mmol) in 10 mL of dry THF was added dropwise to a stirred suspension of 152 mg (4 mmol) of lithium aluminium hydride in 10 mL of dry THF under nitrogen. The reaction mixture was stirred for 19 h. Saturated sodium sulfate solution was added dropwise to the mixture with cooling, and the precipitate was filtered off, and washed with THF. The filtrate was evaporated to dryness, and the product was crystallized from ether-hexane to yield (26), 587 mg; m.p. 68°–70° C.

1',2'-Dihydroxyethyl-9,10-dihydrophenanthrene (27)

A solution of 500 mg of (19) in 15 mL of acetone and 1.5 mL of water was stirred with p-toluenesulfonic acid (165 mg) for 5 h. An additional 330 mg of the acid was added and stirring was continued for 23 h. Then an additional 400 mg of the acid and 1.5 mL of water was added, and stirring was continued for 75 h. The mixture was extracted with ether, the extract was washed with sodium bicarbonate solution, dried, and the solvent was removed to provide crude (27), 509 mg. This was taken up in pyridine (10 mL), treated with acetic anhydride, and the solution was allowed to stand for 21 h at room temperature. The solution was poured into ice-water, the mixture was extracted with ether, washed with 1N HCl and sodium bicarbonate solution, dried, and evaporated to dryness. The diacetate product (570 mg) was dissolved in boiling hexane and chromatographed on a column of Florisil TM. Elution with benzene gave the diacetate. To a solution of the latter (476 mg, 1.47 mmol) in 20 mL of methanol was added a solution of NaOH (235 mg) in 1.5 mL of water and 2 mL of methanol. After standing at room temperature for 16.5 h, this solution was made slightly acidic with acetic acid and worked up conventionally to yield (27), 308 mg. Recrystallization from acetone-hexane gave (27), 233 mg, m.p. 132°–133° C.

EXAMPLE 2

Various methods for measuring receptor binding of radioactive steroid hormones have been described and discussed in detail in a variety of publications including Fang, S., et al., *J. Biol. Chem.*, 246:16 (1971); Liao, S., et al., *J. Biol. Chem.*, 248:6154 (1973); Schilling, et al., *The Prostate*, 5:581 (1984); Liao, S., et al., *Proc. Nat'l. Acad. Sci. (USA)*, 82:8345 (1985). The relative androgen receptor binding activities of some of the compounds of Example 1 were tested. Both the hydroxylapatite-filter assay and the tissue incubation assay were used to measure the ability to compete with radioactive steroid hormones for binding to androgen receptors as described at page 124 of Chang, C., et al., *J. Steroid Biochem.*, 27:123 (1987). The results are presented below in Table 1. The relative binding activity (RBA) is given by:

$$RBA = \frac{IC_{50} \text{ for R1881}}{IC_{50} \text{ for test compound}} \times 100$$

TABLE 1

Relative receptor binding activity (RBA). The effects of test compounds on [$^3$H]R1881 (17α-methyltrienolone) binding to androgen receptor of rat ventral prostate in the cell-free assay system. The concentrations (μM) of test compounds needed to show 50% inhibition (IC$_{50}$) are shown. RBA values are shown in parentheses.

| Compound | IC$_{50}$(μM) |
|---|---|
|  R1881 | 0.02 (100.00) |
|  9,10-dihydrophenanthrene | 10.0 (0.20) |
|  1,2,3,4,5,6,7,8-octahydro-phenanthrene | 200 (0.01) |
|  4'-oxo-7,8-cyclohexeno-9,10-dihydrophenanthren-1-ol (22) | 1.3 (1.53) |
|  17β-estradiol | 1.5 (1.33) |
|  10,11-dihydro-5H-dibenzo-[a,d]cycloheptene | 60.0 (0.03) |
|  phenanthrene | 800 (0.0025) |
|  2-hydroxy-9,10-dihydro-phenanthrene (13) | 7.9 (0.25) |
|  4'-oxo-7,8-cyclohexeno-phenanthren-1-ol (25) | >100 (<0.02) |
|  (±)-6,7,16,17-tetrahydro-15H-cyclo-penta[a]phen-anthren-17-ol (7) | 4.2 (0.48) |

TABLE 1-continued

Relative receptor binding activity (RBA). The effects of test compounds on [³H]R1881 (17α-methyltrienolone) binding to androgen receptor of rat ventral prostate in the cell-free assay system. The concentrations (μM) of test compounds needed to show 50% inhibition (IC$_{50}$) are shown. RBA values are shown in parentheses.

| Compound | IC$_{50}$(μM) |
|---|---|
| (±)-6,7,16,17-tetrahydro-15H-cyclo-penta[a]phenanthren-17-one (6) | 17.8 (0.11) |
| (±)-2-(1'-hydroxyethyl)-9,10-dihydrophenanthrene (9) | 2.6 (0.77) |
| (±)-2-(1'-hydroxyethyl)-9-(or 10)-methyl-9,10-dihydrophenanthrene (11) | 6.8 (0.29) |
| 2-(2'-hydroxyethyl)-9,10-dihydrophenanthrene (26) | 3.6 (0.56) |
| 2-(2',3'-dihydroxyethyl)-9,10-dihydrophenanthrene (27) | 47.9 (0.04) |

The IC$_{50}$ is that concentration needed to give 50% inhibition of 3H-R1818 binding to androgen receptors isolated, as described in Chang, C., et al., *J. Steroid Biochem.*, 27:123 (1987), from rat ventral prostate. Table 1 gives the IC$_{50}$ for reference compounds, including: R1881; 17-β-estradiol; 9,10-dihydrophenanthrene; 10,11-dihydro-5H-dibenzo[a,d]cyclopentene and for compounds of the invention including: 4'-oxo-7,8-cyclohexeno,9,10-dihydrophenanthren-1-ol (22); 1-[2-(9,10-1-ethanol (9); 6,7,16,17(9(or 10)-methyl-9,10-dihydrophenanthryl)]-1-ethanol (11); 2-hydroxy-9,10-dihydrophenanthrene (13); 6,7,16,17-tetrahydro-15H-cyclopental[a]phenanthren-17one (6); 4'-oxo-7,8-cyclohexenophenanthren-1-ol (25); 2(2'-hydroxyethyl)-9,10-dihydrophenanthrene (26); and 2(2',3'-dihydroxyethyl)-9,10-dihydrophenanthrene (27).

An IC$_{50}$ of 10 μM or less is considered most desirable for an effective anti-androgen. The results indicate that the generalized structure (as depicted as page 3) for the most effective anti-androgens are those derivatives which have a flexible structure between, preferably, two aromatic rings. A carbonyl group and/or a hydroxyl group at either end of the compound, as in the case with natural androgens, increases the potency, apparently by increasing the recognition of functional groups in the binding cavity of the androgen receptor.

Because of the possibility that the compounds of the invention may display particularly enhanced activity in certain organs, the assay methods described above, while useful in screening potential anti-androgen candidates, may not show the extent of the relative anti-androgenic potencies of the compounds in organs with different pathogenic conditions. Accordingly, it is anticipated that some of the new compounds, that may not exhibit high activities in the assays shown, may still be useful in the treatment of abnormalities. One way to additionally confirm the effectiveness of the anti-androgens of the present invention is to perform an in vivo anti-androgenic activity assay. Chang, C., et al., *J. Steroid Biochem.*, 27:123 (1987) (legend of Table 2, page 129) (see also "androgenicity assay" on page 6155 of Liao, S., et al., *J. of Biol. Chem.*, 248:6154 (1973). Briefly, the method comprises castrating rats on day one and injecting, with either testosterone propionate and/or a test compound, subcutaneously daily until the 8th day. On the 9th day, the rats are killed and organs, such as the ventral prostate, the seminal vesicle, and the coagulating gland, from individual rats are weighed.

Excessive androgenic activities are implicated in pathogenesis of certain androgen dependent conditions, such as benign prostatic hyperplasia and prostate cancer (Huggins, et al., *Cancer Res.*, 1:293 (1941); Siiteri, et al., *J. Clin. Invest.*, 49:1737 (1970); Geller, et al., *J. Clin. Endocr. Metab.*, 43:686 (1976), acne (Sansone, et al., *J. Invest. Dermat.*, 56:366 (1971)), male pattern baldness (Bingham, et al., *J. Endocr.*, 59:11 (1973); and female hirsutism (Kuttenn, et al., *J. Endocr.*, 25:83 (1977)). The anti-androgens of the invention, are therefore expected to be useful in treating these abnormalities [(Martini, L. and Motta, M., *Androgens and Anti-androgens*, Raven Press, New York (1977)) because many of those abnormalities are due to excess androgens and androgenic activities in the organs affected.

Compounds (active or inactive in the assays shown) can be administered by topical (especially for skin) or internal (oral or injection) routes. In addition, it is expected that some of these compounds may interact with mutated receptors and, therefore, may be useful in the treatment, as well as in the diagnosis of androgen and other hormone-insensitive tumors. The compounds of the invention are also expected to be important in the studies of the mechanism of action of androgens and anti-androgens especially if they are radioactively labelled.

Further, it is anticipated that the compounds of the invention will find utility in localizing androgen receptors. For example, compounds of the invention can be suitably labelled (e.g., with fluorescent groups or radioactive or non-radioactive isotopes) to serve as markers for both in vitro and in vivo analyses of, for example, the tissue distribution of androgen receptors.

The foregoing illustrative examples relate to new classes of anti-androgens, their method of synthesis and use. While the present invention has been described in terms of specific methods and compositions, it is understood that variations and modifications will occur to those skilled in the art upon consideration of the present invention.

For example, it is envisioned that various dihydrophenanthrene derivatives and compounds with steroid ring systems, as described above, will also be effective according to the present invention. Although the preferred compounds are: 6,7,16,17-tetrahydro-15H cyclopenta[a]phenanthren-17-ol (7); 1-[2-(9,10dihydrophenanthryl)]-1-ethanol (9); 1-[2-(9-(or 10)-methyl-9,10-dihydrophenanthryl)]-1-ethanol (11); 2-hydroxy-9,10-dihydrophenanthrene (13); 4'-oxo-7,8 9,10-dihydrophenanthren-1-ol (22); 4'-oxo-7,8-cyclohexenophenanthren-1-ol (25); 2-(2'-hydroxyethyl)-9,10-dihydrophenanthrene (26); and 2-(2',3'-dihydroxyethyl)-9,10-dihydrophenanthrene (27); it is not intended to preclude others, such as 2-[2-(1-naphthyl)ethyl]-cyclopentanone (3); 16,17-dihydro-15Hcyclopenta[ a]phenanthrene (4); 6,7,16,17-tetrahydro-15H-cyclopenta[a]phenanthrene (5); 2-acetyl-9,10dihydrophenanthrene (8); 2-acetyl-9(or 10)-methyl-9,10-dihydrophenanthrene (10); 2-acetoxyphenanthrene (12); 1-(2-hydroxytheyl)-5-methoxynaphthalene (16); 1-methoxy-5,6,10a-tetrahydro-8(9H)benzo[a]phenanthrene-8-one (19); 4'-oxo-7,8-cyclohexeno,9,10-dihydrophenanthren-1-ol propionate (23); and 4'-oxo-7,8-cyclohexeno,9,10-dihydrophenanthren-1-ol acetate (24) from being included in the scope of the present invention.

Also, because the acetate and propionate forms of androgens and anti-androgens have been used effectively in vivo, it is expected that these esters (as well as other ester analogues) are more soluble and metabolically stable and may be more appropriate than the free-alcohol forms for the delivery to the target sites; therefore, these derivatives may be more potent when used as drugs for treating abnormalities and are also contemplated within the scope of the invention.

Numerous modifications and variations in the invention as described in the above illustrative examples are expected to occur to those skilled in the art and consequently only such limitations as appear in the appended claims should be placed thereon.

Accordingly it is intended in the appended claims to cover all such equivalent variations which come within the scope of the invention as claimed.

What is claimed is:

1. A method for treatment of disorders associated with excessive androgenic activity comprising administering a pharmaceutical composition which includes an anti-androgenic compound selected from the group consisting of the general formula:

wherein ring A is 2-substituted with a hydroxyl, a 1'-hydroxyethyl or a 2' hydroxyethyl; ring B is monounsaturated at the 9-10 position and is optionally substituted with methyl at either the 9 or 10 position; and ring C is unsubstiuted, provided that rings A and C may not both be unsubstituted.

* * * * *